United States Patent
Sugita

(10) Patent No.: US 9,102,606 B2
(45) Date of Patent: Aug. 11, 2015

(54) METHOD FOR PRODUCING BRANCHED CHAIN ALDEHYDE

(71) Applicant: MITSUBISHI GAS CHEMICAL COMPANY, INC., Tokyo (JP)

(72) Inventor: Masaki Sugita, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/398,806

(22) PCT Filed: May 8, 2013

(86) PCT No.: PCT/JP2013/062893
§ 371 (c)(1),
(2) Date: Nov. 4, 2014

(87) PCT Pub. No.: WO2013/168726
PCT Pub. Date: Nov. 14, 2013

(65) Prior Publication Data
US 2015/0087864 A1    Mar. 26, 2015

(30) Foreign Application Priority Data
May 10, 2012    (JP) ................................. 2012-108444

(51) Int. Cl.
*C07C 45/50*    (2006.01)
(52) U.S. Cl.
CPC .................................... *C07C 45/505* (2013.01)
(58) Field of Classification Search
CPC ...................................................... C07C 45/50
USPC ....................................................... 568/451
See application file for complete search history.

(56) References Cited

U.S. PATENT DOCUMENTS

| 4,690,912 A | 9/1987 | Paulik et al. |
| 5,237,097 A | 8/1993 | Smith et al. |

FOREIGN PATENT DOCUMENTS

| JP | 5-194300 | 8/1993 |
| JP | 6-262086 | 9/1994 |
| JP | 11-080066 | 3/1999 |
| JP | 2000-256249 | 9/2000 |

OTHER PUBLICATIONS

"Industrial Organic Chemistry Fourth Edition, Tokyo Kagaku Dojin", , 1996, pp. 139.
Luca Rosi et al., "The behaviour of n- and iso-propylcobalt tricarbonyl tributylphosphine complexes under hydroformylation conditions", Journal of Organo Metallic Chemistry, 1997, pp. 143-147.
Xiaowei Zhang et al., "Rhodium-catalyzed Asymmetric Hydroformylation of N-Allylamides: Highly Enantioselective Approach to B2-Amino Aldehydes", Angewandte Chemie, 2010, pp. 4047, vol. 49.
H.K. Reinius et al., "o-Alkyl-Substituted Triphenyl Phosphines: Activity and Regioselectivity in Rhodium-Catalysed Propene Hydroformylation", Journal of Catalysis, 2001, pp. 302, vol. 199.
Search report from PCt/JP2013/062893, mail date is Jun. 4, 2013.
International Preliminary Examination Report in PCT/JP2013/062893 issued Nov. 11, 2014.

*Primary Examiner* — Sikarl Witherspoon
(74) *Attorney, Agent, or Firm* — Greenblum & Bernstein, P.L.C.

(57) ABSTRACT

A method for producing a branched chain aldehyde, comprising: reacting an aliphatic olefin having a double bond at an end with carbon monoxide and hydrogen using an iodide of a Group 9 metal as a catalyst and at least one or more selected from the group consisting of hydrogen iodide and alkyl iodides as a promoter.

8 Claims, No Drawings

METHOD FOR PRODUCING BRANCHED CHAIN ALDEHYDE

FIELD OF THE INVENTION

The present invention relates to a method for producing a branched chain aldehyde using an aliphatic olefin as a raw material.

DESCRIPTION OF THE RELATED ART

Usually, aldehydes are produced by an oxo process in which hydroformylation is performed using an olefin as a raw material. A feature of the oxo process is that a straight chain alkyl aldehyde is preferentially obtained. In the oxo process, a branched chain aldehyde is a by-product, and therefore cannot be produced in a large amount (Non-Patent Literature 1). Particularly, recently, there has been a tendency that the selectivity of a straight chain alkyl aldehyde in the oxo process is increased, and therefore, it has been difficult to obtain a branched chain aldehyde, which is a by-product, inexpensively in a large amount.

It is known that in an oxo process in which styrene is used as a raw material, a branched chain aldehyde is preferentially obtained. However, when an aliphatic olefin, such as propylene, is used as a raw material, it is difficult to preferentially produce a branched chain aldehyde. So far, attempts have been made to develop catalysts with which a branched chain aldehyde can be preferentially produced even if an aliphatic olefin is used as a raw material, but the reactivity has not reached a practical level.

For example, for the purpose of forming an optically active aldehyde by hydroformylation, an attempt has been made to preferentially form a branched chain aldehyde using a complex catalyst comprising a ligand having an asymmetric structure and rhodium (Non-Patent Literature 2). However, in the case of this method, it is necessary to substitute an olefin, which is a raw material, by a functional group for molecular recognition, and therefore, this method cannot be applied to a process for producing a simple aldehyde having no coordinating functional group or the like. In addition, the ligand used is an expensive one having a special structure, and therefore, this method is disadvantageous in terms of cost.

On the other hand, it has been reported that a branched chain aldehyde is formed by performing a reaction under conditions similar to those of hydroformylation using an alkyl halide for a raw material and allowing a stoichiometric amount of tricarbonyltributylphosphinecobaltsodium [NaCo(CO)$_3$(PBu$_3$)] to act as a catalyst (Non-Patent Literature 3). However, this method is not an economical method because a stoichiometrically expensive rhodium complex is used. In addition, there is no description of the conversion rate of the alkyl halide.

In addition, it has been reported that a branched chain aldehyde is selectively obtained by hydroformylating an olefin using as a homogeneous catalyst a complex in which a ligand having at least one nitrogen atom, such as morpholine or hexamethylphosphorustriamide, is coordinated to rhodium (Patent Literature 1).

In addition, a method for improving the selectivity of isobutyraldehyde, which is a branched chain aldehyde, by hydroformylating propylene using a catalyst in which the triphenylphosphine ligand of a rhodium complex is improved has been reported (Non-Patent Literature 4).

PRIOR ART LITERATURES

Patent Literature
  Patent Literature 1: Japanese Patent Laid-Open No. 06-262086
Non-Patent Literatures
  Non-Patent Literature 1: Industrial Organic Chemistry, Fourth Edition, Tokyo Kagaku Dojin, 1996, p. 139
  Non-Patent Literature 2: Angew. Chem. Int. Ed., Vol. 49, 4047 (2010)
  Non-Patent Literature 3: J. Organometallic Chem., Vol. 535, 143 (1997)
  Non-Patent Literature 4: J. Catalysis, vol. 199, 302 (2001)

SUMMARY OF THE INVENTION

Problems to be Solved by the Invention

A problem of the method described in Patent Literature 1 is that when an attempt is made to preferentially obtain the branched chain aldehyde, the reaction activity decreases. Another problem is that when hydroformylation is performed using a complex in which morpholine is coordinated to rhodium, which provides the highest selectivity of the branched chain aldehyde, the raw material conversion rate is less than 3%, and practical catalytic activity is not shown.

In addition, in the method described in Non Patent Literature 4, the proportion of isobutyraldehyde in formed aldehydes is, at the maximum, 53% of that in a case where bis(o-tolyl)phenylphosphine is used for a ligand, and the initial rate of the reaction at this time decreases significantly, one eighteenth compared with an industrially used catalyst comprising triphenylphosphine as a ligand. In addition, a disadvantage is that as much as 47% of n-butyraldehyde is also formed, and therefore, as much as 47% or more of propylene, a raw material, is lost. Further, a problem is that with an increase in the selectivity of isobutyraldehyde, the reaction activity of the catalyst decreases. Therefore, in this method, the branched chain aldehyde cannot be efficiently produced.

As described above, a method for preferentially forming a branched chain aldehyde without decreasing reaction activity has not been developed so far, and a new technique that can economically produce a branched chain aldehyde has been required. In other words, it is an object of the present invention to provide a method for efficiently and economically producing a branched chain aldehyde useful as a raw material for medicines, agricultural chemicals, polymers, and the like.

Means for Solving the Problems

The present inventors have studied methods for efficiently producing branched chain aldehydes, and addressed the improvement of hydroformylation using an aliphatic olefin, such as propylene, as a raw material. However, it has become clear that in the hydroformylation using an aliphatic olefin as a raw material, it is difficult to produce a branched chain aldehyde with sufficient reaction activity kept, and there is a limit to the improvement of the selectivity of the branched chain aldehyde due to the steric hindrance of the reaction intermediate. Therefore, the present inventors have paid attention to hydroformylation using for a raw material an aliphatic alkyl halide having a branched chain alkyl structure, instead of an aliphatic olefin. However, no aldehydes have been obtained under the same reaction conditions as the conventional hydroformylation using an aliphatic olefin as a raw material when an aliphatic alkyl halide is used for a raw material.

The present inventors have further diligently studied over and over, and, as a result, found that by using an iodide of a Group 9 metal as a catalyst and further allowing one or more selected from the group consisting of hydrogen iodide and alkyl iodides to coexist as a promoter, such hydroformylation that a branched chain aldehyde is preferentially formed proceeds even if an aliphatic olefin is used as a raw material, and achieved the present invention.

Specifically, the present invention relates to a production method shown in the following [1] to [8].

[1] A method for producing a branched chain aldehyde, comprising: reacting an aliphatic olefin having a double bond at an end with carbon monoxide and hydrogen using an iodide of a Group 9 metal as a catalyst and at least one or more selected from the group consisting of hydrogen iodide and alkyl iodides as a promoter.

[2] The method for producing the branched chain aldehyde according to the above [1], wherein the Group 9 metal is rhodium or iridium.

[3] The method for producing the branched chain aldehyde according to the above [1], wherein the Group 9 metal is rhodium.

[4] The method for producing the branched chain aldehyde according to any of the above [1] to [3], wherein the alkyl iodide is represented by the following chemical formula (I):

$$CH_3CHI-R \qquad (I)$$

wherein R represents an alkyl group having 1 to 6 carbon atoms, and a total number of carbon atoms in the formula is the same as number of carbon atoms of the aliphatic olefin.

[5] The method for producing the branched chain aldehyde according to any of the above [1] to [4], wherein an amount of the promoter used is 1 to 300 mol % based on the aliphatic olefin.

[6] The method for producing the branched chain aldehyde according to any of the above [1] to [5], wherein the aliphatic olefin is an aliphatic olefin having a double bond at an end and having 3 to 8 carbon atoms.

[7] The method for producing the branched chain aldehyde according to any of the above [1] to [6], wherein the iodide of a Group 9 metal is rhodium iodide.

[8] The method for producing the branched chain aldehyde according to any of the above [1] to [7], wherein the aliphatic olefin is propylene.

Advantageous Effects of the Invention

According to the present invention, in hydroformylation using an aliphatic olefin for a raw material, a branched chain aldehyde can be preferentially produced without decreasing reactivity.

In addition, the method for producing a branched chain aldehyde according to the present invention is an economically advantageous method, and further does not require investment, which is an excessive load, because a production facility of the conventional oxo process can be used.

MODE FOR CARRYING OUT THE INVENTION

A mode for carrying out the present invention (hereinafter also simply referred to as "this embodiment") will be described in detail below. The present invention is not limited to this embodiment below, and various modifications can be made without departing from the scope and spirit thereof.

A method for producing a branched chain aldehyde in this embodiment is a production method comprising reacting an aliphatic olefin having a double bond at an end with carbon monoxide and hydrogen using an iodide of a Group 9 metal as a catalyst and at least one or more selected from the group consisting of hydrogen iodide and alkyl iodides as a promoter.

[Aliphatic Olefin]

In the method for producing a branched chain aldehyde in this embodiment, an aliphatic olefin having a double bond at an end (hereinafter also simply referred to as an "aliphatic olefin") is used as a raw material. The aliphatic olefin is not particularly limited, however, aliphatic olefins having a double bond at an end and having 3 or more carbon atoms are preferred in terms of preferentially forming the branched chain aldehyde. For example, when propylene is used for a raw material, isobutyraldehyde, which is a branched chain aldehyde, is preferentially formed. In addition, when 1-pentene is used for a raw material, 2-methylpentanal is preferentially formed. Among them, aliphatic olefins having a double bond at an end and having 3 to 8 carbon atoms are more preferred. In addition, even if the aliphatic olefin has a double bond within the hydrocarbon chain in addition to at an end, hydroformylation proceeds specifically to the double bond site at the end, and therefore, the branched chain aldehyde can be obtained.

The aliphatic olefin includes for example, but not particularly limited, propylene, 1-butene, 1-pentene, 1-hexene, 1-heptene, 1-octene, 1,3-pentadiene, 1,3-hexadiene, and 1,4-hexadiene. However, when the aliphatic olefin also has a double bond within the hydrocarbon in addition to at the end, the isomerization of the internal double bond also proceeds, and therefore, the product behavior become complicated. Therefore, aliphatic olefins having a double bond only at an end and having 3 to 8 carbon atoms are more preferred as a raw material. Examples of such aliphatic olefins include propylene, 1-butene, 1-pentene, 1-hexene, 1-heptene, and 1-octene.

[Catalyst]

In the method for producing a branched chain aldehyde in this embodiment, an iodide of a Group 9 metal is used as a catalyst. The Group 9 metal is preferably at least one or more selected from the group consisting of cobalt, rhodium, and iridium, and is more preferably at least one or more selected from the group consisting of rhodium and iridium, further preferably rhodium, in terms of preferentially forming the branched chain aldehyde. In addition, the iodide of a Group 9 metal may be an anhydride or may have water of crystallization.

For the catalyst, the Group 9 metal, the catalyst, is preferably used in the range of 0.0001 to 100 mol %, more preferably in the range of 0.001 to 10 mol %, based on the aliphatic olefin, which is a raw material. When the amount of the catalyst used is 0.0001 mol % or more, there is a tendency that the reactivity is good. On the other hand, when the amount of the catalyst used is 100 mol % or less, there is a tendency that the removal of the catalyst is easy, and impurities derived from the catalyst can be prevented from being mixed in the obtained branched chain aldehyde.

[Promoter]

In the method for producing a branched chain aldehyde in this embodiment, at least one or more selected from the group consisting of hydrogen iodide and alkyl iodides is used as a promoter. When hydrogen iodide is used, either form of hydriodic acid or a hydrogen iodide gas may be used, or both may be simultaneously used. When an alkyl iodide is used, an alkyl iodide having the same number of carbon atoms as the aliphatic olefin, a raw material, is preferably used in terms of improving the purity of the product. Among them, alkyl iodides having a branched chain alkyl are more preferred. Alkyl iodides represented by the following chemical formula (I) are further preferred because there is a tendency that the selectivity and purity of the branched chain aldehyde is further improved.

  (I)

wherein R represents an alkyl group having 1 to 6 carbon atoms, and the total number of carbon atoms in the formula is the same as the number of carbon atoms of the aliphatic olefin.

The alkyl group having 1 to 6 carbon atoms represented by R is not particularly limited, and examples thereof include a methyl group, an ethyl group, a n-propyl group, an isopropyl group, a t-butyl group, a cyclopropyl group, and a cyclopentyl group. Among them, a methyl group and an ethyl group are preferred in terms of improving reaction activity.

The amount of the promoter used during the reaction is preferably 1 to 300 mol %, more preferably 5 to 50 mol %, based on the aliphatic olefin, which is a raw material. When the amount of the promoter used is 1 mol % or more, there is a tendency that the reaction proceeds with the selection rate of the branched chain aldehyde kept high. On the other hand, when the amount of the promoter used is 300 mol % or less, there is a tendency that the reaction can be allowed to proceed without the precipitation of iodine occurring. When no precipitation of iodine occurs during the reaction, it is not necessary to separate iodine, and therefore, the purification of the branched chain aldehyde become easy, and further, metal corrosion due to iodine precipitation is also suppressed.

[Charge and Solvent]

In the method for producing a branched chain aldehyde in this embodiment, for example, a batch type pressure-resistant reactor or the like is charged with the aliphatic olefin, which is a raw material, the catalyst, and the promoter, and then, hydrogen and carbon monoxide are brought into contact with the contents in the reactor to carry out hydroformylation. At this time, a solvent may be used for the purpose of increasing the amounts of the aliphatic olefin, the hydrogen gas, and the carbon monoxide to be charged, or for the purpose of improving the efficiency of the contact of the aliphatic olefin, the catalyst, the promoter, the hydrogen gas, and the carbon monoxide.

The solvent is not particularly limited, but those having low reaction activity with the aliphatic olefin, the catalyst, the promoter, the hydrogen gas, and the carbon monoxide are preferred in terms of preventing side reactions due to the solvent. In addition, in terms of improving the reaction rate, polar solvents are preferred. Examples of solvents satisfying both properties include water-soluble ethers, such as tetrahydrofuran, 1,4-dioxane, diglyme, cellosolve, methyl cellosolve, and ethyl cellosolve.

In terms of further improving the reaction rate, water is preferably contained in the water-soluble ether to the extent that the solubility of the aliphatic olefin is not significantly lost. The solvent used in the reaction, and the amount of water contained in the solvent may be appropriately determined according to the solubility of the aliphatic olefin used. However, if the amount of the solvent is too large, the aldehyde formation rate decreases, and the amounts of aldehydes formed based on the amount of a reaction liquid decreases. Therefore, the amount of the solvent used is preferably 1000 times by mass or less, more preferably 100 times by mass or less, and further preferably 20 times by mass or less, based on the aliphatic olefin, which is a raw material.

[Hydroformylation]

In this embodiment, the branched chain aldehyde is produced by reacting the aliphatic olefin with carbon monoxide and hydrogen for hydroformylation. The hydroformylation is carried out by bringing a hydrogen gas and a carbon monoxide gas into contact with the contents in the reactor described above in a state of being heated to 80 to 200° C. The hydrogen gas and the carbon monoxide gas may be separately fed, or may be fed as a mixed gas.

The pressures of the hydrogen gas and the carbon monoxide gas in the reactor are each preferably 0.5 to 20 MPa. When the pressures of the hydrogen gas and the carbon monoxide are each 0.5 MPa or more, there is a tendency that the aldehyde formation rate can be kept well. On the other hand, when the pressures of the hydrogen gas and the carbon monoxide are each 20 MPa or less, there is a tendency that side reactions of hydrogenation can be suppressed, and a decrease in the activity of the catalyst due to the coordination of carbon monoxide can be avoided.

The progress of the reaction can be checked by observing changes in pressure over time by a pressure gauge mounted in the reactor. For example, the point of time when the pressure reaches equilibrium can be determined as the end point of the reaction.

[Posttreatment of Reaction Liquid]

After the completion of the reaction, a reaction liquid comprising the aldehydes can be obtained by discharging the residual gas out of the reactor after cooling the reactor to less than the boiling points of the formed aldehydes. The branched chain aldehyde can be recovered from the reaction liquid by a known method, such as distillation. The unreacted aliphatic olefin, the hydrogen gas, and the carbon monoxide gas contained in the residual gas may be used in the reaction again after recovery. In addition, the catalyst and the promoter remaining after aldehyde recovery can also be recycled in the reaction after purification.

Isobutyraldehyde, which has been difficult to preferentially obtain by the conventional oxo process, can be preferentially produced by the production method in this embodiment using, for example, propylene, as a raw material. Isobutyraldehyde has a wide range of uses as a raw material for medicines, agricultural chemicals, polymers, and the like.

EXAMPLES

Next, the present invention will be more specifically described by Examples and Comparative Examples, but the present invention is not limited only to these Examples.

Propylene, a raw material, and aldehydes, which were reaction products, were subjected to quantitative analysis under the following gas chromatography (GC) conditions.

[Quantitative Analysis of Propylene]

Column: Gaskuropak-54 (3 mm I. D.×4 m, 80/100 mesh) manufactured by GL Sciences and Porapak-S (3 mm I. D.×4 m, 80/100 mesh) manufactured by GL Sciences are connected in series Sample injection port temperature: 110° C.

Sample injection method: the gas is directly introduced from the gas phase portion of a reactor via a 2 mL sample loop Detector: TCD Detector temperature: 150° C. (110 mA)

Carrier gas: helium

Carrier gas flow rate: 240 kPa (pressure control)

Column temperature: the temperature is maintained at 110° C. for 25 minutes, then increased to 140° C. at 10° C./min, and maintained at 140° C. for 30 minutes Quantification: absolute calibration method

[Quantitative Analysis of Aldehydes]

Column: HP-1 (0.32 mm I. D.×30 m, film thickness 0.25 μm) manufactured by Agilent Technologies Sample injection port temperature: 200° C.

Sample injection method: the reaction liquid is diluted 5 times with tetrahydrofuran, an internal standard is added, and then the mixture is injected by a split method (split ratio 100:1)

Detector: TCD

Detector temperature: 250° C.

Carrier gas: helium

Carrier gas flow rate: 2.0 mL (flow rate control)

Column temperature: the temperature is maintained at 40° C. for 5 minutes, then increased to 250° C. at 10° C./min, and maintained at 250° C. for 5 minutes Quantification: an internal standard method using heptane as an internal standard Example 1

A 20 mL zirconium autoclave was charged with 0.024 g (0.050 mmol, 1 mol % based on propylene) of rhodium iodide, 0.11 g (0.49 mmol, 10 mol % based on propylene) of 57% hydriodic acid and 1.4 mL of tetrahydrofuran under nitrogen, and then, 0.21 g (5.0 mmol) of propylene was fed. Further, a mixed gas having a hydrogen/carbon monoxide volume ratio of 1/1 was fed to the autoclave until the pressure reached 6 MPa. While stirring was performed by an electromagnetic stirrer, the autoclave was heated at 150° C. for 3 hours. After the heating, the autoclave was cooled to 0° C., and the gas in the reactor was discharged to obtain a reaction liquid comprising aldehydes.

When the gas in the reactor after the completion of the reaction was quantitatively analyzed by GC, the conversion rate of propylene was 36%. In addition, when the aldehydes in the reaction liquid were quantitatively analyzed by GC, 0.078 g (1.1 mmol) of isobutyraldehyde and 0.0492 g (0.68 mmol) of n-butyraldehyde were present. The formation ratio of isobutyraldehyde to n-butyraldehyde (I/N) was 1.6, and isobutyraldehyde was preferentially formed. In addition, the loss of propylene due to conversion to n-butyraldehyde, which was not the target isobutyraldehyde, was only 14%.

Example 2

A 20 mL zirconium autoclave was charged with 0.024 g (0.050 mmol, 1 mol % based on propylene) of rhodium iodide, 0.085 g (0.50 mmol, 10 mol % based on propylene) of 2-iodopropane, and 1.4 mL of tetrahydrofuran under nitrogen, and then, 0.21 g (5.0 mmol) of propylene was fed. Then, a reaction was performed by a method similar to that of Example 1 to obtain a reaction liquid comprising aldehydes.

When the gas in the reactor after the completion of the reaction was quantitatively analyzed by GC, the conversion rate of propylene was 60%. In addition, when the aldehydes in the reaction liquid were quantitatively analyzed by GC, 0.130 g (1.8 mmol) of isobutyraldehyde and 0.085 g (1.2 mmol) of n-butyraldehyde were present. The formation ratio of isobutyraldehyde to n-butyraldehyde (I/N) was 1.5, and isobutyraldehyde was preferentially formed. In addition, the loss of propylene was only 24%.

Example 3

A 20 mL zirconium autoclave was charged with 0.024 g (0.050 mmol, 1 mol % based on propylene) of rhodium iodide, 0.085 g (0.50 mmol, 10 mol % based on propylene) of 2-iodopropane, 1.4 mL of tetrahydrofuran, and 0.048 g of water under nitrogen, and then, 0.21 g (5.0 mmol) of propylene was fed. Then, a reaction was performed by a method similar to that of Example 1 to obtain a reaction liquid comprising aldehydes.

When the gas in the reactor after the completion of the reaction was quantitatively analyzed by GC, the conversion rate of propylene was 43%. In addition, when the aldehydes in the reaction liquid were quantitatively analyzed by GC, 0.101 g (1.4 mmol) of isobutyraldehyde and 0.054 g (0.75 mmol) of n-butyraldehyde were present. The formation ratio of isobutyraldehyde to n-butyraldehyde (I/N) was 1.9, and isobutyraldehyde was preferentially formed. In addition, the loss of propylene was only 15%.

Example 4

A 20 mL zirconium autoclave was charged with 0.024 g (0.050 mmol, 1 mol % based on propylene) of rhodium iodide, 0.085 g (0.50 mmol, 10 mol % based on propylene) of 2-iodopropane, 0.11 g (0.49 mmol, 10 mol % based on propylene) of 57% hydriodic acid, and 1.4 mL of tetrahydrofuran under nitrogen, and then, 0.21 g (5.0 mmol) of propylene was fed. Then, a reaction was performed by a method similar to that of Example 1 to obtain a reaction liquid comprising aldehydes.

When the gas in the reactor after the completion of the reaction was quantitatively analyzed by GC, the conversion rate of propylene was 9%. In addition, when the aldehydes in the reaction liquid were quantitatively analyzed by GC, 0.025 g (0.35 mmol) of isobutyraldehyde and 0.0054 g (0.075 mmol) of n-butyraldehyde were present. The formation ratio of isobutyraldehyde to n-butyraldehyde (I/N) was 4.6, and isobutyraldehyde was preferentially formed. In addition, the loss of propylene was only 1.5%.

Comparative Example 1

A 20 mL zirconium autoclave was charged with 0.024 g (0.050 mmol, 1 mol % based on propylene) of rhodium iodide and 1.4 mL of tetrahydrofuran under nitrogen, and 0.21 g (5.0 mmol) of propylene was fed. Then, a reaction was performed by a method similar to that of Example 1 to obtain a reaction liquid comprising aldehydes.

When the gas in the reactor after the completion of the reaction was quantitatively analyzed by GC, the conversion rate of propylene was 69%. In addition, when the aldehydes in the reaction liquid were quantitatively analyzed by GC, 0.104 g (1.44 mmol) of isobutyraldehyde and 0.144 g (2.0 mmol) of n-butyraldehyde were present. The formation ratio of isobutyraldehyde to n-butyraldehyde (I/N) was 0.72, and n-butyraldehyde was preferentially formed. In addition, 40% of propylene was lost.

Comparative Examples 2 to 6

A 20 mL zirconium autoclave was charged with a catalyst shown in Table 1, 0.11 g (0.49 mmol, 10 mol % based on propylene) of 57% hydriodic acid, and 1.4 mL of tetrahydrofuran under nitrogen, and then, 0.21 g (5.0 mmol) of propylene was fed. Then, a reaction was performed by a method similar to that of Example 1 to obtain a reaction liquid.

When aldehydes in the reaction liquid were quantitatively analyzed by GC, no formation of aldehydes was observed in the cases where any catalyst was used.

Comparative Examples 7 and 8

A 20 mL zirconium autoclave was charged with a catalyst shown in Table 1, 0.085 g (0.50 mmol, 10 mol % based on propylene) of 2-iodopropane, and 1.4 mL of tetrahydrofuran under nitrogen, and then, 0.21 g (5.0 mmol) of propylene was fed. Then, a reaction was performed by a method similar to that of Example 1 to obtain a reaction liquid.

When aldehydes in the reaction liquid were quantitatively analyzed by GC, no formation of aldehydes was observed in the cases where any catalyst was used.

The catalysts, promoters, and reaction results in Examples 1 to 4 and Comparative Examples 1 to 8 are shown in Table 1.

This application is based on Japanese Patent Application No. 2012-108444 filed with the Japan Patent Office on May 10, 2012, the content of which is incorporated herein by reference.

TABLE 1

| | Catalyst[a] | Promoter | Charge ratio of promoter to substrate [mol %] | Propylene conversion rate [%] | Amount of isobutyraldehyde formed [mmol] | and yield of isobutyraldehyde [%] | Amount of n-butyraldehyde formed [mmol] | and yield of n-butyraldehyde [%] | Formation ratio (I/N)[c] |
|---|---|---|---|---|---|---|---|---|---|
| Example 1 | Rhodium iodide | 57% hydriodic acid | 10 | 36 | 1.1 | 22 | 0.68 | 14 | 1.6 |
| Example 2 | Rhodium iodide | 2-Iodopropane | 10 | 60 | 1.8 | 36 | 1.2 | 24 | 1.5 |
| Example 3 | Rhodium iodide | 2-Iodopropane[b] | 10 | 43 | 1.4 | 28 | 0.75 | 15 | 1.9 |
| Example 4 | Rhodium iodide | 2-Iodopropane 57% hydriodic acid | 10 10 | 8.5 | 0.35 | 7 | 0.075 | 1.5 | 4.6 |
| Comparative Example 1 | Rhodium iodide | None | — | 69 | 1.44 | 29 | 2.0 | 40 | 0.72 |
| Comparative Example 2 | Nickel iodide | 57% hydriodic acid | 10 | 0 | 0 | 0 | 0 | 0 | — |
| Comparative Example 3 | Palladium iodide | 57% hydriodic acid | 10 | 0 | 0 | 0 | 0 | 0 | — |
| Comparative Example 4 | Platinum iodide | 57% hydriodic acid | 10 | 0 | 0 | 0 | 0 | 0 | — |
| Comparative Example 5 | Ruthenium iodide | 57% hydriodic acid | 10 | 0 | 0 | 0 | 0 | 0 | — |
| Comparative Example 6 | Iron iodide | 57% hydriodic acid | 10 | 0 | 0 | 0 | 0 | 0 | — |
| Comparative Example 7 | Platinum iodide | 2-Iodopropane | 10 | 0 | 0 | 0 | 0 | 0 | — |
| Comparative Example 8 | Ruthenium iodide | 2-Iodopropane | 10 | 0 | 0 | 0 | 0 | 0 | — |

(Remarks)
[a]The catalyst was used at the amount of 1 mol % based on the propylene, the substrate.
[b]The reaction was performed in the coexistence of 0.048 g of water.
[c]the molar ratio of the amount of isobutyraldehyde formed/the amount of n-butyraldehyde formed As is clear from the results shown in Table 1, by using rhodium iodide as a catalyst and at least one or more selected from the group consisting of hydrogen iodide and alkyl iodides as a promoter, isobutyraldehyde, a branched chain aldehyde, was preferentially formed (Examples 1 to 4), which was difficult by the conventional oxo process. Here, it can be presumed that also in cases where iodides of Group 9 metals other than rhodium (iridium and cobalt) are used as a catalyst, the similar effect described above is obtained.

On the other hand, even in the case where rhodium iodide was used as a catalyst, a straight chain aldehyde was preferentially formed as in the conventional oxo process when at least one or more selected from the group consisting of hydrogen iodide and alkyl iodides was not added as a promoter (Comparative Example 1). In addition, in the cases where iodides of metals other than Group 9 metals were used as a catalyst, the reaction did not proceed and no aldehydes were formed even if hydrogen iodide or an alkyl iodide was added (Comparative Examples 2 to 8).

INDUSTRIAL APPLICABILITY

In the conventional oxo process in which an aliphatic olefin is used for a raw material, the productivity of a branched chain aldehyde has been low because a straight chain aldehyde is selectively formed. But, according to the present invention, a branched chain aldehyde can be produced with high selectivity using an aliphatic olefin for a raw material, even in a production facility similar to that in the conventional oxo process.

The invention claimed is:

1. A method for producing a branched chain aldehyde, comprising reacting an aliphatic olefin having a double bond at an end with carbon monoxide and hydrogen using an iodide of a Group 9 metal as a catalyst and at least one or more selected from the group consisting of hydrogen iodide and alkyl iodides as a promoter.

2. The method for producing the branched chain aldehyde according to claim 1, wherein the Group 9 metal is rhodium or iridium.

3. The method for producing the branched chain aldehyde according to claim 1, wherein the Group 9 metal is rhodium.

4. The method for producing the branched chain aldehyde according to claim 1, wherein the alkyl iodide is represented by the following chemical formula (I):

$$CH_3CHI\text{—}R \qquad (I)$$

wherein R represents an alkyl group having 1 to 6 carbon atoms, and a total number of carbon atoms in the formula is the same as number of carbon atoms of the aliphatic olefin.

5. The method for producing the branched chain aldehyde according to claim 1, wherein the promoter is used at an amount of 1 to 300 mol % based on the aliphatic olefin.

6. The method for producing the branched chain aldehyde according to claim 1, wherein the aliphatic olefin is an aliphatic olefin having a double bond at an end and having 3 to 8 carbon atoms.

7. The method for producing the branched chain aldehyde according to claim 1, wherein the iodide of a Group 9 metal is rhodium iodide.

8. The method for producing the branched chain aldehyde according to claim 1, wherein the aliphatic olefin is propylene.

* * * * *